(12) United States Patent
Laux et al.

(10) Patent No.: US 10,046,151 B2
(45) Date of Patent: Aug. 14, 2018

(54) TRANSDERMAL THERAPEUTIC SYSTEM WITH ELECTRONIC COMPONENT

(71) Applicant: LTS Lohmann Therapie-Systeme AG, Andernach (DE)

(72) Inventors: Wolfgang Laux, Diez (DE); Beatrix Platt, Hausten (DE); Nico Reum, Andernach (DE)

(73) Assignee: LTS Lohmann Therapie-Systeme, AG, Andernach (DE)

( * ) Notice: Subject to any disclaimer, the term of this patent is extended or adjusted under 35 U.S.C. 154(b) by 0 days.

(21) Appl. No.: 14/975,478

(22) PCT Filed: Jul. 3, 2014

(86) PCT No.: PCT/EP2014/064166
§ 371 (c)(1),
(2) Date: Dec. 18, 2015

(87) PCT Pub. No.: WO2015/001012
PCT Pub. Date: Jan. 8, 2015

(65) Prior Publication Data
US 2016/0220800 A1    Aug. 4, 2016

(30) Foreign Application Priority Data

Jul. 3, 2013  (EP) .................................. 13174880

(51) Int. Cl.
| | | |
|---|---|---|
| *A61M 37/00* | (2006.01) | |
| *A61K 9/70* | (2006.01) | |
| *A61F 13/02* | (2006.01) | |
| *A61K 9/00* | (2006.01) | |
| *A61K 45/06* | (2006.01) | |
| *A61F 13/00* | (2006.01) | |
| *A61F 13/84* | (2006.01) | |

(52) U.S. Cl.
CPC ............. *A61M 37/00* (2013.01); *A61F 13/02* (2013.01); *A61F 13/0259* (2013.01); *A61K 9/0097* (2013.01); *A61K 9/703* (2013.01); *A61K 45/06* (2013.01); *A61F 2013/00906* (2013.01); *A61F 2013/0296* (2013.01); *A61F 2013/8479* (2013.01); *A61M 2205/3592* (2013.01); *A61M 2207/00* (2013.01)

(58) Field of Classification Search
None
See application file for complete search history.

(56) References Cited

U.S. PATENT DOCUMENTS

| | | | | |
|---|---|---|---|---|
| 2004/0131897 A1* | 7/2004 | Jenson | ................ | H01M 2/0267 429/7 |
| 2009/0048556 A1* | 2/2009 | Durand | ................ | A61K 9/0009 604/20 |
| 2010/0311661 A1* | 12/2010 | Kullertz | ................ | A61K 31/45 514/16.4 |

FOREIGN PATENT DOCUMENTS

| | | |
|---|---|---|
| WO | WO 00/44437 | 8/2000 |
| WO | WO 2005/119610 | 12/2005 |

\* cited by examiner

*Primary Examiner* — Robert A Wax
*Assistant Examiner* — Quanglong N Truong
(74) *Attorney, Agent, or Firm* — Haug Partners LLP

(57) ABSTRACT

Transdermal therapeutic systems are described which have at least one electronic component, as well as methods for producing this type of transdermal therapeutic systems.

10 Claims, 1 Drawing Sheet

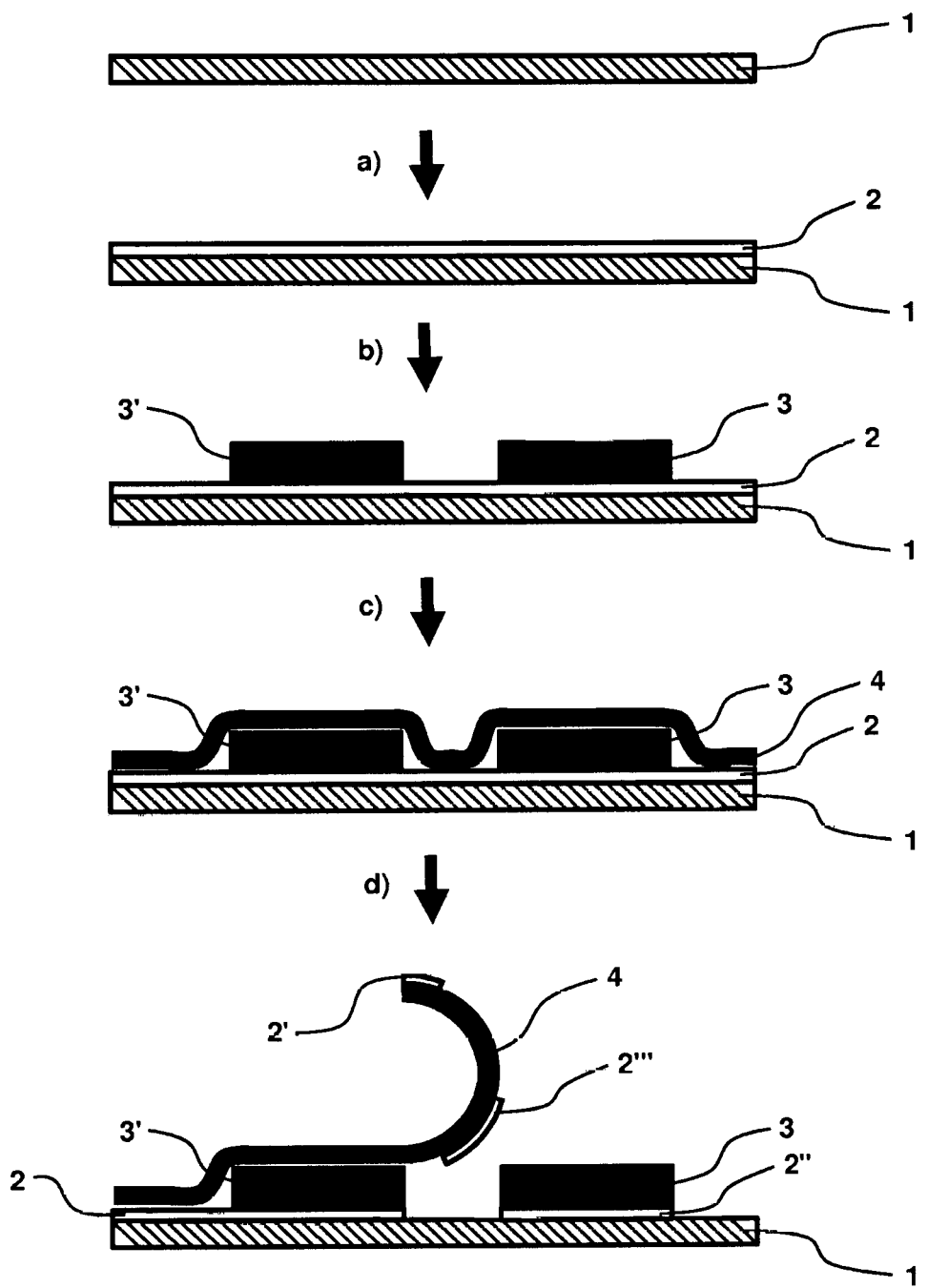

TRANSDERMAL THERAPEUTIC SYSTEM WITH ELECTRONIC COMPONENT

The present application claims priority from PCT Patent Application No. PCT/EP2014/064,166, filed on Jul. 3, 2014, which claims priority from European Patent Application No. EP 13174880.8 filed on Jul. 3, 3013, the disclosures of which are incorporated herein by reference in their entirety.

The invention relates to transdermal therapeutic systems and methods for manufacturing the same. The invention in particular relates to transdermal therapeutic systems which comprise at least one electronic component.

A transdermal therapeutic system in the following description refers to a device for administering one or more active agents, in particular one or more pharmaceutical active agents, via the intact skin of a mammal. Transdermal therapeutic systems are planar devices which contain at least one active agent and are fastened on the skin or at the skin of a mammal, preferably on or at the skin of a human, so that the active agent contained in the device can be administered to and through the skin of the mammal over a longer period of time at a constant or at least at an approximately constant rate. The attachment of a transdermal therapeutic system at or on the skin of a patient can be effected by means of a bandage or at least an adhesive strip. In particular embodiments the transdermal therapeutic systems, however, are equipped with a pressure-sensitive adhesive. This means that they have a pressure-sensitive surface by means of which they can be adhered to the skin of the mammal and which ensures a long-term contact of the device with the skin of the mammal.

In one embodiment of the transdermal therapeutic systems, the pressure-sensitive surface is formed from a pressure-sensitive polymer matrix which also contains the active agent or at least one of the active agents. In an further and/or alternative embodiment the pressure-sensitive surface is a separate adhesive layer which is applied to at least a portion of the skin-side surface of the transdermal therapeutic system, preferably on the skin-side surface of the active agent reservoir.

The at least one active agent reservoir of a transdermal therapeutic system is either a polymer matrix in which the at least one active agent is included, or a bag-like reservoir which is limited by a shell and contains a substantially liquid active agent preparation. The term "liquid" also encompasses highly fluid, viscous and gel-like preparations. The shell of the bag-like reservoir at least on the side facing to the skin comprises a semi-permeable membrane via which the active agent contained in the reservoir can be discharged and which optionally has a function of controlling the release rate of the active agent. If the at least one active agent is included in a polymer matrix of the transdermal therapeutic system, said polymer matrix has to be considered as an active agent reservoir A transdermal therapeutic system includes at least one active agent, preferably at least one pharmaceutical active agent. The at least one pharmaceutical active agent may be any transdermally administrable pharmaceutical active agent. For example, anticholinergics, parasympatholytics, antimycotics, MAO-B inhibitors, serotonin antagonists, alpha2 receptor agonists, photosensitizers, hormones and/or proteins may be used as pharmaceutical active agents. In one embodiment the at least one pharmaceutical active agent is selected from the group of active agents consisting of 5-aminolevulinic acid, buprenorphine, capsaicin, clonidine, fentanyl, granisetron, glyceryl trinitrate, hydromorphone, memantine, oxybutynin, rivastigmine, rotigotine, selegiline and sertaconazole. The at least one pharmaceutical active agent is provided in the form of its free base and/or at least one of its pharmaceutically acceptable salts. The term "pharmaceutically acceptable salt" also includes pharmaceutically acceptable acid addition salts of the active agent. Provided that the at least one active agent is a chiral substance the active agent is present in the transdermal therapeutic system either in the form of a racemate or in form of its pharmaceutically active enantiomer.

In one embodiment transdermal therapeutic systems comprise an active agent impermeable backing layer. In an additional and/or alternative embodiment the transdermal therapeutic systems include a removable protective layer which covers the pressure-sensitive surface of the transdermal therapeutic system prior to its application. The removable protective layer has to be removed from the pressure-sensitive surface prior to the application of the transdermal therapeutic system.

In a first aspect the invention relates to transdermal therapeutic systems which include at least one electronic component.

In a second aspect the invention relates to methods for producing transdermal therapeutic systems which include at least one electronic component.

According to the first aspect the invention relates to transdermal therapeutic systems which comprise at least one electronic component. In one embodiment the at least one electronic component is a passive component, i.e. an electronic component that is not provided with an own power supply.

In an alternative embodiment the at least one electronic component is an active component. Active electronic components in contrast to passive electronic components are provided with an own power supply. In particular embodiments the at least one active electronic component includes at least one voltage source which serves as a power supply of the electronic component. The at least one voltage source may be a solar cell, a capacitor or a galvanic element, for example, a battery or a secondary battery.

According to particular embodiments the at least one electronic component is selected from the group of electronic components consisting of transmitters, receivers, data storages, sensors and measuring instruments.

In a particular embodiment the at least one electronic component is a radio tag. The radio tag may be selected from the group of electronic components consisting of transponders, passive RFID transponders (RFID=radio frequency identification), active RFID transponders, semi-active RFID transponders and semi-passive RFID transponders. Each transponder comprises a microchip, an antenna and a support or housing. Active transponders in addition include the power source. The structure of a RFID transponder in principle includes an antenna, an analog circuit for receiving and transmitting (transceiver) and a digital circuit and a non-volatile memory. The digital circuit in complex models is a small microcontroller.

RFID transponders include an at least write-once memory, which contains their inalterable identity. If rewritable memories are used additional information can be stored during the lifespan.

In particular embodiments the electronic component allows to identify and optionally locate the transdermal therapeutic system which includes the electronic component. The transponder of radio tags is used for storing and/or transferring data. For example, data stored on a transponder can be transferred to a device which is adapted to receive, process, optionally store and display this data. In particular embodiments, the transponder allows storing and/or reading information that may be used for therapy optimization and/or therapy monitoring. Information that can be used for therapy optimization and/or therapy monitoring may be information indicating which agent is contained within the transdermal therapeutic system and in what dosage, when the transdermal therapeutic system has been applied, when the applied transdermal therapeutic system should be removed, when a new transdermal therapeutic system should be applied and if the transdermal therapeutic system is properly attached to the patient or is detached. In a preferred embodiment, the information associated with the time of application, the application duration and/or the intended end time of the application of the transdermal therapeutic system is generated by the activation of the radio tag by means of the contact of the transdermal therapeutic system with the skin.

The electronic component may vary in size and shape. In one embodiment the electronic component is provided in the form of a non-flexible element having a thickness of between approximately 10 μm to approximately 1.5 mm.

In one embodiment the at least one electronic component is applied on the backing layer of the transdermal therapeutic system. This arrangement provides the advantage that prefabricated transdermal therapeutic systems can be provided with an electronic component.

In another embodiment the at least one electronic component is integrated in the transdermal therapeutic system. This means that the at least one electronic component is embedded, for example, in an active agent containing polymer matrix. In an additional and/or alternative embodiment the at least one electronic component is disposed between two matrix layers or between the active agent reservoir and the active agent impermeable backing layer. These embodiments have the advantage that the electronic component becomes an integral part of the transdermal therapeutic system and it is not possible to remove the electronic component without destroying the transdermal therapeutic system.

According to the second aspect the invention relates to a method for producing transdermal therapeutic systems which include at least one electronic component, preferably a radio tag.

In the method according to the second aspect of the invention the electronic components are manufactured separately and the transdermal therapeutic systems are provided with at least one of the prefabricated electronic components either during or after their manufacture. This means in a first embodiment that at least one prefabricated electronic component is mounted on a prefabricated transdermal therapeutic system. In another and/or alternative embodiment at least one prefabricated electronic component is mounted on a not yet fully prefabricated transdermal therapeutic system. In a yet other and/or alternative embodiment at least one prefabricated electronic device is integrated into the transdermal therapeutic system during its manufacture.

In the former embodiment at least one separately produced electronic component is mounted on the backing layer of a prefabricated transdermal therapeutic system or its immediate precursor. To this end, in one variant of this embodiment first a process film is coated on the entire surface with a pressure-sensitive adhesive. In a further step, the electronic components are placed on the adhesive layer and then covered with a cover film. Subsequently, the cover film is peeled off again, wherein the pressure-sensitive adhesive in the areas where no electronic components are placed, is removed with the peeling off of the cover film from the process film. The process film loaded with the electronic components is converted into rolls or in another embodiment subjected to fanfolding. In a further process step the individual electronic components including the adhesive layer adhering to them are transferred onto transdermal therapeutic systems or their immediate precursor by means of a labeling machine.

Prefabricated transdermal therapeutic systems refer to already separated, ready for use transdermal therapeutic systems, i.e. transdermal therapeutic systems that already have their intended surface. Immediate precursors of transdermal therapeutic systems refer to the laminate of the active agent impermeable backing layer, the active agent containing reservoir and the removable protective layer, from which the individual transdermal therapeutic systems are separated by cutting or punching.

The method according to the first embodiment thus comprises:
coating a process film with a pressure-sensitive adhesive,
applying prefabricated electronic components onto the adhesive layer,
covering or lining the adhesive layer and the electronic components applied thereon with a cover film,
removing the cover film,
converting the process film loaded with the electronic components into a roll material or fanfolding the process film loaded with the electronic components,
dispensing the electronic components from the process film loaded with the electronic components by a labeling machine, and
transferring the electronic components onto transdermal therapeutic systems or their immediate precursor.

The process film comprises at least one surface which is dehesive with respect to the adhesive which is to be coated onto the process film. For pressure-sensitive silicone adhesives preferably perfluorinated process films are used. Preferred process films for pressure-sensitive silicone adhesives are, for example, the polyester films commercially available on the filing date of the present disclosure under the trade name Scotchpak™ from 3M Company, St. Paul, Minn. Particularly preferred perfluorinated process films include, for example, the polyester films sold under the trade names Scotchpak™ 1022 and Scotchpak™ 9755 which are coated with fluoropolymer, so that according to the manufacturer's information a "liner release" of <1.0 N/25.4 mm (for Scotchpak™ 1022) or <0.4 N/25.4 mm (for Scotchpak™ 9755) results. Preferred process films which are to be coated with a hydrophilic pressure-sensitive adhesive, for example, a hydrophilic pressure-sensitive acrylate adhesive or a polyisobutylene, in contrast, have a siliconized surface. A process film suitable for hydrophilic pressure-sensitive adhesives is, for example, siliconized paper.

The process film is coated with a pressure-sensitive adhesive. The coating is preferably applied on the entire surface. The coating of the process film with the pressure-sensitive adhesive is carried out such that an adhesive film with a substantially uniform thickness is formed. The thickness of the adhesive film is at least about 10 μm, preferably about 30 μm. The thickness of the adhesive film, however, should not be greater than about 500 μm, and preferably should not exceed a thickness of about 200 μm. An adhesive film of this thickness allows for a safe and precise positioning of the electronic components without causing an undesirably large lateral movement of the electronic components applied onto the process film, as well as a reliable tearing of the adhesive film at the edges of the electronic components when the cover film is peeled off.

The electronic components are preferably the aforementioned radio tags/transponders.

The cover film may be any polymer film, to which the pressure-sensitive adhesive adheres. Suitable cover films consist for example of a polyester such as polyethylene terephthalate. The cover film must be flexible so that it can be pulled over a deflector roll or an edge when it is peeled off. Preferably, the cover film is peeled off while forming an acute angle.

In the method the process film, the adhesive and the cover film are to be selected so that the adhesive adheres more strongly to the cover film than to the process film and the adhesive film tears during the removal of the cover film at the edges of the applied electronic components.

When covering the adhesive layer and the electronic components applied onto the adhesive layer with the cover film the adhesive adheres in those areas at the cover film, in which it is not covered with the electronic components. During the subsequent removal of the cover film the adhesive film adhering to it in the areas where it is not covered by electronic components is peeled off from the process film. Thereby, the adhesive film tears at the edges of the electronic components applied onto the adhesive film, so that the electronic components are not peeled off together therewith but remain on the process film including the areas of the adhesive film covered by them. In this way, a process film loaded with electronic components is obtained which essentially has no free adhesive areas which could affect the further use of the process film then converted into rolls or stacks.

The process film loaded with electronic components is converted into rolls or formed into a stack by fanfolding. Thus the process film loaded with electronic components can be supplied to a labeling machine, by means of which the electronic components coated with the adhesive film can be transferred to transdermal therapeutic systems or their immediate precursor in an automated process step.

The transfer of electronic components coated with an adhesive layer from the process film to transdermal therapeutic systems or their immediate precursor can be implemented manually or by machine. The transfer by machine can be carried out as described above by means of a labeling machine. In a different approach, the individual electronic components can be grasped by a robotic arm, removed from the process foil and placed on the transdermal therapeutic systems or their immediate precursor.

It is basically possible to transfer the electronic components onto already finished, i.e. already separated, transdermal therapeutic systems. In another embodiment, the individual electronic components are transferred onto the immediate precursor of the transdermal therapeutic systems, i.e. onto a laminate, which comprises an active agent impermeable backing layer, at least one active agent containing reservoir and optionally already a detachable protective layer. After transferring the electronic components onto the laminate the individual transdermal therapeutic systems are separated so that they comprise at least one of the electronic components. The separation of the transdermal therapeutic systems is implemented, for example, by punching or cutting out the individual transdermal therapeutic systems from the laminate.

In another implementation of the first embodiment electronic components not provided with adhesive are transferred onto transdermal therapeutic systems or their immediate precursor. In this implementation at least one adhesive area per transdermal therapeutic system is applied onto the backing layer of the transdermal therapeutic system or the immediate precursor by means of screen printing. In this procedure adhesive areas are attached substantially at the positions of the transdermal therapeutic systems or their immediate precursor at which electronic components are to be mounted. The applied adhesive areas have substantially the same surface area and shape as the electronic components to be mounted.

In this implementation the electronic components to be transferred have not to be provided with a pressure-sensitive adhesive, since the adhesive necessary for mounting the electronic components is applied onto the active agent impermeable backing layer. In this embodiment, too, the electronic components can be transferred onto the transdermal therapeutic systems or their immediate precursor manually or by machine. In a variant of the transfer by machine, for example, electronic components stacked in a tube are transferred from below from a dispenser onto transdermal therapeutic systems by means of an arm provided with a vacuum suction cup arm. In another variant the individual electronic components are gripped by a robot arm, preferably gripped laterally and positioned on an adhesive area on the backing layer of a transdermal therapeutic system or its immediate precursor.

In another embodiment at least one electronic component is integrated in a transdermal therapeutic system. This means that the at least one electronic component is disposed between two layers of a multi-layered transdermal therapeutic system, for example, between two active agent containing layers or between the active agent containing reservoir and the active agent impermeable backing layer. Alternatively or additionally at least one electronic component can be embedded in a polymer layer of the transdermal therapeutic system.

In one implementation of this embodiment prefabricated electronic components are not transferred onto the already finished transdermal therapeutic systems, but integrated into transdermal therapeutic systems during their manufacture, for example by applying the electronic components onto the last produced layer of a laminate and subsequently covering them with a further layer. For example, the electronic components are placed directly onto an active agent containing polymer layer, which forms the active agent containing polymer matrix or a part of the active agent containing polymer matrix in the finished transdermal therapeutic system and is covered by another active agent containing polymer layer, an active agent free polymer layer or an active agent impermeable backing layer. If the layer onto which the electronic components are placed is a pressure-sensitive adhesive layer the electronic components need not to be provided with a pressure-sensitive adhesive area. If the layer on which the electronic components are placed, is not a pressure-sensitive adhesive layer, the electronic components can be provided with a pressure-sensitive adhesive area, for example, similar to the former embodiment. In a later process step at least one further layer, for example at least one further active agent containing polymer layer and/or an active agent impermeable backing layer is applied onto the layer provided with electronic components and the individual transdermal therapeutic systems are separated from the resulting laminate such that each individual transdermal therapeutic system comprises at least one electronic component.

This embodiment has the advantage that the at least one electronic component is disposed between an active agent containing polymer matrix and an active agent impermeable backing layer and thus cannot be removed from the transdermal therapeutic system without destroying it.

In a further implementation of this embodiment at least one electronic component is embedded in a polymer matrix. In this case, the electronic component can be cast or pressed into a polymer matrix before a further layer, for example a further matrix layer or the active agent impermeable backing layer is applied onto the polymer matrix.

Hereinafter one embodiment of the method according to the invention is explained in more detail with reference to the figures. It should be noted that the figures are merely illustrative and shall in no way restrict the scope of the invention.

FIG. 1 is a schematic diagram of some process steps in one embodiment of the method for producing transdermal therapeutic systems which comprise an electronic tag.

First, a web of siliconized paper was provided as a process film 1. The process film 1 was coated in a process step a) on an entire surface with an adhesive layer 2. The adhesive was poly[(2-ethyl hexyl) acrylate-co-methyl acrylate-co-acrylic acid-co-(2,3-epoxypropyl)methacrylate](61.5:33:5.5:0.02). This pressure-sensitive acrylate adhesive is commercially available under the trade name DuroTak® 2353 from National Starch, now Henkel. The thickness of the adhesive layer 2 on the process films 1 was 30 μm. Then, radio tags 3, 3' were placed on the adhesive layer 2 (process step b). In a subsequent process step (step c), the radio tags 3, 3' and the remaining free surface of the adhesive layer 2 were covered with a polyethylene terephthalate film as a cover film 4. In the areas where the cover film 4 came into contact with the adhesive layer 2, the cover film 4 adhered to the adhesive layer 2. Then, in step d) the cover film 4 was peeled off again. Thereby the areas 2', 2''' of the adhesive layer 2 which were in contact with the cover film 4 adhered to the cover film 4 and were peeled off together with the cover film 4. The areas 2'' of the adhesive layer 2 covered by the radio tags 3, 3' did not adhere to the cover film 4. When removing the cover film 4 the areas of the adhesive layer 2 adhering to the cover film 4 were separated from the areas of the adhesive layer which were covered by the radio tags 3, 3'. In this way, the radio tags 3, 3' remained on an adhesive layer on the process film 1 which was coextensive with their base surface.

The invention claimed is:

1. A method for producing a transdermal therapeutic system comprising at least one electronic component, including the steps of:
    coating a process film with a pressure-sensitive adhesive;
    applying prefabricated electronic components onto the adhesive layer;
    covering the adhesive layer and the electronic components applied thereon with a cover film;
    removing the cover film, wherein the adhesive and the cover layer are selected so that the adhesive adheres more strongly to the cover film than to the process film and the adhesive film tears during the removal of the cover film at the edges of the applied electronic components;
    converting the process film with the electrical components applied thereon into a roll or fanfolding the process film loaded with the electronic components; and
    transferring the electronic components onto transdermal therapeutic systems or their immediate precursor.

2. The method according to claim 1;
    wherein the cover film is pulled over a deflector roll or an edge during the removal.

3. The method according to claim 1;
    wherein the dispensing of the electronic components is implemented by means of a labeling machine.

4. A method for producing a transdermal therapeutic system comprising at least one electronic component, including the steps of:
    applying at least one electronic component onto one of the layers of a laminate which is included in the finished transdermal therapeutic system;
    covering the electronic components applied onto the one layer of the laminate with a further layer, which is also included in the finished transdermal therapeutic system; and
    separating individual transdermal therapeutic systems.

5. The method according to claim 4;
    wherein the application of the at least one electronic component is carried out by means of a mechanical arm provided with a vacuum cup or by means of a gripper.

6. The method according to claim 4;
    wherein the layer onto which the at least one electronic component is applied is an active agent containing reservoir or an active agent impermeable backing layer in the finished transdermal therapeutic system.

7. The method according to claim 4;
    wherein the further layer, with which the electronic components applied onto one layer of the laminate is covered, is an active agent containing polymer layer, an active agent free polymer layer, or an active agent impermeable backing layer of the finished transdermal therapeutic system.

8. A method for producing a transdermal therapeutic system comprising at least one electronic component, including the step of
    embedding at least one electronic component in an active agent containing polymer matrix by casting or pressing the at least one electronic component into a layer forming the polymer matrix.

9. The method according to claim 2;
    wherein the cover film is pulled over the deflector roll or the edge during the removal by forming an acute angle.

10. The method according to claim 6;
    wherein the layer onto which the at least one electronic component is applied is the active agent containing reservoir, which is an active agent containing matrix layer.

* * * * *